(12) United States Patent
Lang et al.

(10) Patent No.: US 6,696,554 B2
(45) Date of Patent: Feb. 24, 2004

(54) PRODUCTION OF POLYGALACTURONIDES AND THEIR USE AS FOOD ADDITIVES

(75) Inventors: Christine Lang, Berlin (DE); Heike Dörnenburg, Berlin (DE)

(73) Assignee: Technische Universitat Berlin, Berlin (DE)

( * ) Notice: Subject to any disclaimer, the term of this patent is extended or adjusted under 35 U.S.C. 154(b) by 3 days.

(21) Appl. No.: 10/009,055

(22) PCT Filed: Apr. 6, 2001

(86) PCT No.: PCT/EP01/03998

§ 371 (c)(1),
(2), (4) Date: Feb. 25, 2002

(87) PCT Pub. No.: WO01/76609

PCT Pub. Date: Oct. 18, 2001

(65) Prior Publication Data

US 2003/0013678 A1 Jan. 16, 2003

(30) Foreign Application Priority Data

Apr. 6, 2000 (DE) .......................... 100 19 076

(51) Int. Cl.[7] .............................................. C08B 37/06
(52) U.S. Cl. ...................................................... 536/2
(58) Field of Search ............................... 536/2; 426/50, 426/658; 435/201, 232, 18, 19, 72, 74; 514/54

(56) References Cited

U.S. PATENT DOCUMENTS 4,191,744 A * 3/1980 Bogentoft .................... 424/78
4,211,799 A * 7/1980 Grampp et al. ............... 426/50

OTHER PUBLICATIONS

Voragen, A.G.J. "Technological aspects of functional food-related carbohydrates", Trend Food Sci. Technol. 9, 328–335, 1998.*
Matsumoto, T. et al "The Pectic Polysaccharide From Bupleurum Falcatum L. Enhances Immune–Complexes Binding To Peritoneal Macrophages Through Fc Receptor Expression", Int. J. Immunopharmacol. 15, 683–693, 1993.*

* cited by examiner

Primary Examiner—James O. Wilson
Assistant Examiner—Ganapathy Krishnan
(74) Attorney, Agent, or Firm—Rothwell Figg Ernst & Manbeck

(57) ABSTRACT

The invention relates to the use of polygalacturonides as food additives, said polygalacturonides being obtainable via the following process steps:

a) a pectinous plant material is subjected to a pectin extraction in aqueous solution;

b) the solids are removed from the suspension obtained in step a), consisting of liquid phase including dissolved pectin and solids from the plant material;

c) the pectin is precipitated from the liquid phase obtained in step b);

d) the pectin obtained in step c) is dissolved in an aqueous solution and cleaved with purified endo-polygalacturonase;

e) the polygalacturonides obtained in step d) are processed into a polygalacturonide preparation without using an additional separation step and without hydrolyzing ester groups that are present.

31 Claims, No Drawings

PRODUCTION OF POLYGALACTURONIDES AND THEIR USE AS FOOD ADDITIVES

BACKGROUND OF THE INVENTION

The invention relates to polygalacturonides and to the use thereof. Polygalacturonides are oligosaccharides obtained e.g by enzymatic decomposition of pectins. Pectin has galacturonic acid monomers or galacturonic acid (methyl) ester monomers as major components. Typically, both monomers are present at the same time, the esterification level of the galacturonic acid groups ranging from 0.5% to 70%. The galacturonic acid monomers or ester monomers are $\alpha$-1,4-linked to each other. In particular regions of the pectin molecule, however, rhamnose monomers are inserted in the chain, resulting in a zigzag structure of the polymer. The rhamnose monomers may have side chains attached thereto which may be formed of arabans ($\alpha$-1,5 linkage) and arabinogalactans (linkage: $\beta$-1, 3-1, 6-D). The side chains may also include other sugar monomers. As a supplement, reference is made to the "Flüssiges Obst" Jun. 1997, pp. 301. This citation also describes that the use of pectinases in juice production for clarification purposes gives rise to undesirable colloids which interfere with further processing and must be removed or prevented. In natural unfiltrated juices, on the other hand, it is only the pectins rather than the fragments thereof which have an advantageous influence on the viscosity. It is clear from these considerations that in juice production, for example, the presence of pectin fragments is undesirable for technical reasons.

In addition to technical aspects, pectins also involve physiological aspects. The citation Cerda, J. J., Trans. Am. Clin. Climatol. Assoc. 99, 203–213 (1987), describes that pectin from grapefruits plays an important role in promoting health in consumers. The citation Matsumoto, T. et al, Int. J. Immunopharmacol. 15, 683–693 (1993), describes that particular fragments of Bupleuran 2IIc, a pectin-like polysaccharide from the roots of *Bupleurum falcatum*, might be highly important in pharmaceutical terms. The fragments are obtained by reaction with endo-polygalacturonase (EC 3.2.1.15). Ultimately, the citation Voragen, A. G. J., Trends Food Sci. Technol. 9, 328–335 (1998), provides information that non-digestible polysaccharides or oligosaccharides may have a number of health-promoting effects on persons consuming same.

Producing oligosaccharides for pharmaceutical purposes from pectins using pectinases is known from the citation U.S. Pat. No. 5,683,991. The pectinases used therein are mixtures of various enzymes which possibility also include endo-polygalacturonase (EC 3.2.1.15), so that cleavage also is effected in the side chain regions. Moreover, the ester groups are hydrolyzed prior to reacting with the pectinases so that, as a result, comparatively small oligosaccharides (2–4 monomers) are obtained.

SUMMARY OF THE INVENTION

Additives in the food industry are to fulfill a variety of functions. Essential functions are in the sector of preparing processed foodstuffs, e.g. with respect to consistency, durability and color appearance.

The invention is based on the technical problem of providing an additive for foods which would improve the foods in a health-promoting respect, with respect to taste, and optionally with respect to consistency and/or other consumer-related properties.

To solve said technical problem, the invention teaches the use of polygalacturonides as additives in goods, said polygalacturonides being obtainable via the following process steps:

1. a pectinous plant material is subjected to a pectin extraction is aqueous solution;
2. the solids are removed from the suspension obtained in step a), consisting of liquid phase including dissolved pectin and solids from the plant material;
3. the pectin is precipitated from the liquid phase obtained in step b);
4. the pectin obtained in step c) is dissolved in an aqueous solution and cleaved with purified endo-polygalacturonase (EC 3.2.1.15);
5. the polygalacturonides obtained in step d) are processed into a polygalacturonide preparation with using an additional separation step and without hydrolyzing ester groups that are present.

DETAILED DESCRIPTION OF THE EMBODIMENTS

Within the range of the invention, it is essential that no hydrolysis of ester groups takes place and that, owing to the use of purified endo-polygalacturonase (EC 3.2.1.15), only bonds in (naturally) non-esterified galacturonic acid monomer units undergo cleavage. As a result, a higher amount of comparatively large oligosaccharides, e.g., with 5–20 monomer units (main and optionally side chains), is obtained. Here, virtually all of the polygalacturonides are saturated polygalacturonides, they are less reactive compared to the unsaturated polygalacturonides formed by pectin lyase or pectate lyase activity and therefore do not contribute to non-enzymatic browning and formation of hydroxymethyl-furfural (HMF) from fructose or glucose. The mixture of various oligosaccharide structures thus obtained has distinct advantages. On the one hand, fragments with largely retained side chains have a supporting effect on the immune system in physiological terms. In addition, the comparatively long oligosaccharides of the invention assume a roughage effect, as is the case with other long-chain polyers as well. Roughage is important in the prophylaxis and therapy of a number of diseases such as constipation, diverticulosis, colon carcinoma, diabetes mellitus, and lipid metabolic diseases. However, the drawbacks of conventional roughage, namely, binding of essential nutrients, will be reduced when using oligosaccharides of the invention ranging from 5 to 20 monomer units. Moreover, by virtue of the intestinal bacterial flora as found in organisms, the polygalacturonides according to the invention are converted relatively readily to short-chain fatty acids such as acetate, butyrate and propionate which in turn have a positive effect on the intestinal flora and on the intestinal pH value. These fatty acids can be utilized energetically by the organism (energy content of the basic oligosaccharides: about 2 kcal/g), serving particularly mucosa blood circulation as well. In addition, the polygalacturonides used according to the invention have an antibacterial and emulsion-stabilizing effect, which is particularly advantageous in food-technological terms. This also enables the use as fat substitutes, e.g., in mayonnaises and the like.

The use according to the invention can be effected with a wide variety of processed foods, such as ready meals, baby food, canned food (including food filled in glassware), such as canned vegetables and canned fruits, beverages, candy and pastry (including chips and the like). In addition to plants themselves, vegetable extraction residues, e.g. from juice production, as well as vegetable cell cultures are possible as pectinous plant material. Plants suitable for use as pectin source can be exemplified as follows:

Any type of fruits, particularly apples and citrus fruits, vegetables, particularly sugar beets, carrots and tomatoes. The pectin extraction can be effected in the neutral (pH 6.0–8.0) or acidic range (pH 2.0–3.0; acid: e.g. sulfuric acid, hydrochloric acid, phosphoric acid, citric acid, lactic acid, and/or tartaric acid). Typical process conditions are as follows:

40–120° C., preferably 90–100° C., 1–20 hours, preferably 6–10 hours, optionally multiple repetitions, e.g. twice.

The solids can be removed by (e.g. hydraulic) pressing and/or centrifugation. Prior to further processing, the resulting solution can be concentrated using vacuum evaporation and/or ultrafiltration.

The pectin precipitation can be effected in a variety of ways. On the one hand, water-miscible organic (non-ionic) solvents can be used, removing the hydrate cage from the pectin, so as to cause precipitation. For example, acetone and $C_1$–$C_{10}$ alkylalcohols are possible, with ethanol being preferred from a food-technological view. Alternatively or additionally, inorganic salts such as sulfates and/or phosphates of aluminum, copper and/or calcium can be employed.

Preferably, step d) is performed using a pH of from 1.4 to 8.2, more preferably from 3.5 to 5.0. The endo-polygalacturonase (EC 3.2.1.15) which is used can be recovered from plants or from microorganisms occurring therein, e.g., cotton/*Aspergillus flavus*/*Aspergillus parasiticus*, rye/*Claviceps purpurea*, maize/*Cochliobolus carbonum*/*Fusarium monilifonne*, American walnut/*Cryphonectria parasitica*, tomato/*Fusarium oxysporum*/*Ralstonia (Pseudonomas) solanacearum*, rice/*Rhizoctonia solani*, grass/*Sclerotinia borealis*, sun flower/*Sclerotinia sclerotiorum*, and apple/*Stereum pureum*, carrot/*Ertwinia carotorova* or *Burkholderia (Pseudomonas) cepacia*, or from microorganisms genetically engineered so as to produce a well-defined endo-polygalacturonase (EC 3.2.1.15). The latter is preferred for its comparatively easy purification. In addition to well-known genes of the above-exemplified microorganisms, well-known cDNAs or cDNAs from plants themselves which encode well-known enzyme structures are possible for recombinant operations. Examples of well-known plant cDNAs are those from *Arabidopsis thaliana*, *Persea americanus* and *Prunus persica*. Examples of well-known endo-polygalacturonase (EC 3.2.1.15) of plants are those from *Lycopersicon esculentum, Musa acuminata, Gossypium barbadense, Gossypium hirsutum, Cucumus sativus, Phaseolus vulgaris, Citrus limon, Mangifers indica, Cucumis melo, Passiflora edulis, Prunus persica, Pyrus communis, Rubus idaeus*, and *Fragaria ananassa*. It is preferred to use one or more endo-polygalacturonase (EC 3.2.1.15) selected from the endo-polygalacturonase (EC 3.2.1.15) which can be obtained from organisms of the group consisting of *Aspergillus carbonarius, Aspergillus niger, Aspergillus oryzae, Aspergillus tubingensis, Aspergillus ustus, Kluyveromyces marxianus, Neurospora crassa, Penicillium frequentans*, and *Saccharomyces cerevisiae* SCPP, *Lactobacillus casei, Lactobacillus plantarum, Lactococcus lactis, Bacteroides thetaiotaomicron, Piromonas communis, Neocalimastix patriciarum*, or from other microorganisms modified with DNA sequences of the above organisms which encode the endo-polygalacturonase (EC 3.2.1.15). The purification can be effected using e.g. the gel filtration technology which is well-known to those skilled in the art. The amount of endo-polygalacturonase (EC 3.2.1.15) employed in step d) advantageously ranges from 10 to 1000, preferably from 20 to 400 U/g pectin. Determination of the activity is effected using the following method:

10 mg/l polygalacturonic acid (e.g. Sigma P 7276, according to the product specification valid on Mar. 01, 2000) is dissolved in substrate buffer (2 mM citric acid solution, 1 mM $CaCl_2$) and added with defined quantity of enzyme solution. Incubation is effected for 15 min at 23° C. The reaction then is stopped by adding an equal volume of 4.4 mM 2-hydroxy-3, 5-dinitrobenzoic acid solution, boiling for 5 min, and cooling to 0° C. Eventually, the absorption at 540 nm is detected, and the conversion is determined from these values against a standard curve in the usual manner. One unit is the conversion of 1 $\mu$M of galacturonic acid per minute.

In a particularly preferred embodiment of the invention, the endo-polygalacturonase (EC 3.2.1.15) is immobilized by inclusion in enzyme membrane reactors, e.g. flat membrane or hollow fiber membrane reactors, or binding to a conventionally prepared support material can be effected in an absorptive, ionic chelating, covalent way, or by crosslinking.

The immobilization allows to make sure that the final product is virtually free of endo-polygalacturonase (EC 3.2.1.15) and, in fact, without an extra separation. In this way, interfering reactions due to otherwise possible entraining of the employed endo-polygalacturonase (EC 3.2.1.15) with pectins possibility included in the food is virtually excluded. In particular, this is advantageous because undesirable decomposition of pectins included in the foods might have an unfavorable effect on the consistency of the foods, e.g. the viscosity thereof. Moreover, the endo-polygalacturonase (EC 3.2.1.15) consumption is comparatively low.

The reaction with endo-polygalacturonase (EC 3.2.1.15) in step d) preferably is effected at 4 to 80° C., more preferably 30 to 70° Cm, for 2 to 300 min, preferably 45 to 150 min. The operations can be performed in a continuous or discontinuous (batchwise) fashion. As to the continuous process, the above-mentioned time period relates to the average residence time in a reaction volume containing endo-polygalacturonase (EC 3.2.1.15).

The polygalacturonides according to the invention are employed at concentrations of from 0.01 to 1.0 g/kg food, preferably from 0.1 to 0.5 g/kg food. The concentration should be adjusted with regard to normal human food consumption so as to maintain doses of from 0.5 to 50 mg, preferably from 1 to 25 mg per kg body weight per day.

With reference to the examples which merely represent embodiments, the invention will be illustrated in more detail below.

EXAMPLE 1

Isolation and purification of a endo-polygalacturonase (EC 3.2.1.15) from tomatoes.

Tomatoes, 1 kg, are homogenized in 1 liter (l) of water, and the suspension obtained is adjusted to pH 3.0. The solids (cell residues) are removed by centrifugation (10,000 g, 20 min) and washed in water. The pellets are taken up to 50 mM sodium acetate/1.25 mM NaCl (ph 6.0) at 4° C. for 1 hour. Proteins are precipitated by means of 70% ammonium sulfate saturation and removed by centrifuging (10,000 g, 20 min). The protein pellet is dissolved in 0.125 M sodium acetate (pH 6.0) and dialyzed against said buffer. The proteins then are separated on a CM Sepharose column in a 2-stage gradient (0.45 M sodium acetate, pH 6.0, and 1.0 M sodium acetate, pH 6.0). The endo-polygalacturonase (EC 3.2.1.15) elutes with the first stage.

EXAMPLE 2

Preparation and purification of a endo-polygalacturonase (EC 3.2.1.15) from genetically engineered microorganisms.

Yeast (*Saccharomyces cerevisiae*) is transformed using an expression plasmid including cDNA of the *Aspergillus niger* endo-polygalacturonase (EC 3.2.1.15) gene under yeast ADH1 promoter control.

The plasmid still includes the yeast replication origin and yeast selection marker (e.g. LEU2 gene). The yeast strain obtained is pre-grown in nutrient medium (minimal medium) and cultured in a fermentation process wherein the endo-polygalacturonase (EC 3.2.1.15) is discharged into the nutrient medium.

The yeast cells are harvested from 500 ml of medium (centrifuging: 6000 g, 10 min).

The clear medium supernatant is transferred on a carboxymethylcellulose cation exchange column and equilibrated with 10 mM sodium acetate (pH 4.0). The proteins are eluted using a linear gradient of from 1 to 1.5 M NaCl in 10 mM sodium acetate (pH 4.0). Fractions including. pure endo-polygalacturonase (EC 3.2.1.15) elute between 0.6 and 0.75 M NaCl.

EXAMPLE 3
Isolation and Purification of a Polygalacturonase From a Commercially Available Pectinase 50 g of a commercially available enzyme mixture is dissolved in 200 ml of 0.02 M sodium acetate (pH 3.6) with stirring for 3 hours. Solid components are removed by centrifuging (25,000 g, 10 min). The solution then is desalted using a Sephadex g 50 column. The proteins are transferred on an alginate column (matrix by crosslinking alginate with epichlorohydrin) and equilibrated with 0.02 M sodium acetate (pH 3.6). Elution is effected using 0.1 M sodium acetate, pH 4.2, then pH 5.6, and subsequently using a linear NaCl gradient of from 0 to 1 M in acetate buffer, pH 5.6.

The endo-polygalacturonase (EC 3.2.1.15) is eluted in the salt gradient.

EXAMPLE 4
Immobilization of a Polygalacturonase 3 g of a particulate carrier, e.g. silicate or glass carrier derivatized with surface-bound $NH_2$ groups (Solvay Enzymes, Hanover), is suspended in 20 ml of 0.01 M Sørensen phosphate buffer (pH 7.0) and degassed. 0.2 g, i.e. 1000 U of endo-polygalacturonase (EC 3.2.1.15) from Example 3 is dissolved in 5 ml buffer, pH 7.0, and added to the carrier suspension. With stirring, the decline of the extinction at 280 nm is monitored for about 30 to 60 min. The solution is removed, followed by washing 5 times with water, and coupling is effected by adding 10 ml of glutaric dialdehyde solution (5%) and stirring for 30 min. Thereafter, this is washed 5 times in water, 1 hour, followed by washing 3 times with buffer (pH 5.0). Finally, this is suspended in 50 ml of buffer, pH 5.0, to obtain covalently immobilized endo-polygalacturonase (EC 3.2.1.15).

EXAMPLE 5
Preparation of Oligogalacturonides from *Bupleurum falcatum*

Washed roots of *Bupleurum falcatum*, 1 kg, are chopped mechanically and subjected to an extraction process step using 30 kg of deionized water. The extraction is performed twice for 8 hours at 98° C. and atmospheric pressure. Following cooling below 60° C., the suspension obtained is centrifuged (4000 g for 10 min.) to remove solids. The clear supernatant obtained is concentrated to 1/10 of the original volume using vacuum evaporation.

The pectin is precipitated by adding 4 parts by weight of ethanol (96%) per part by weight of solution and separated from the liquid phase by centrifuging (10,000 g for 10 min) at 4° C., optionally with subsequent dialysis. The pectin obtained then is dissolved in a 0.1 M sodium acetate buffer (pH 4.2) and reacted with 300 U/g pectin employed of endo-polygalacturonase (EC 3.2.1.15)(from *Aspergillus japonicus*, available from the Sigma Company under the product designation P 3304, according to the product specifications valid on Mar. 01, 2000) for 4 hours at 37° C., said reaction being done batchwise. The polygalacturonides obtained are recovered in solid form by evaporating the water.

EXAMPLE 6
Preparation of Galacturonides from Beet Pressed Chips

Beet pressed chips, 1 kg, from the beet-processing industry are extracted in 15 kg of an acidic aqueous solution (phosphoric acid, pH 1.5) for 1 hour at 90° C., Following cooling to 20° C., the solid phase is removed by hydraulic pressing and optional filtration. Using vacuum evaporation, this is concentrated to 1/10 the volume of the liquid phase. The pectin is precipitated by adding 2 parts by weight of isopropanol per part by weight of concentrate. Following centrifugation (10,000 g, 10 min) and drying (70° C., 1 hour), the enzymatic hydrolysis is accomplished by adding an aqueous solution of 5 g/kg water (adjusted to pH 4.0) of pectin extract with 20 U/g pectin of endo-polygalacturonase (EC 3.2.1.15) from Example 1 and performing the reaction for 60 min at 60° C. The polygalacturonides obtained are recovered in solid form by evaporating the water.

EXAMPLE 7
Production of Baby Food Containing Polygalacturonides

A ready-to-eat baby food processed as a mash is mixed homogeneously with 0.1 g/kg mash of polygalacturonides from Example 6, and the mash then is packaged in a ready-for-sale fashion. The mash proves to be emulsion-stabilized.

EXAMPLE 8
Production of a Soft Drink Containing Polygalacturonides

A tea is prepared from green tea leaves in the usual manner. Following cooling, 1 g/kg beverage of polygalacturonides from Example 5 are added to the tea to form a solution. The ready-to-bottle product thus obtained has an agreeably sour taste.

EXAMPLE 9
Immobilization by Crosslinking 500 mg of endo-polygalacturonase (EC 3.2.1.15) is dissolved in 15 ml of distilled water. With stirring in an ice bath, 30 ml of ice 3-cold acetone is slowly added, followed by addition of 2 ml of a 25% glutaric dialdehyde solution. Thereafter, this is agitated for 60 min at 30° C. and subsequently centrifuged. The supernatant is discarded, and the residue is stirred up with 40 ml of distilled water and homogenized using an Ultra Turrax. Following centrifugation and discarding of the supernatant, the residue is washed once more with 40 ml of distilled water. The crosslinked preparation obtained is suspended to make 100 ml.

EXAMPLE 10
Fractionation of Polygalacturonides 1.5 g of the polygalacturonides from Example 6 are dissolved in 15 ml of distilled water. The polygalacturonides are separated using chromatography. The solution is transferred on an anion exchange column (2.5/40 cm, BioRad AGMP 1) 150 ml in volume, equilibrated with eluent (0.2 M sodium formate buffer, pH 4.7). The polygalacturonides are eluted using a linear gradient between 0.2 and 0.7 M sodium formate buffer (pH 4.7).

The composition of the individual fractions is subsequently analyzed using thin layer chromatography (TLC). The fractions are transferred on the stationary phase, Silicagel 60 (Merck); a mixture of one part ethanol and one part acetate (25 mM) is used as mobile phase. The development is performed at 35° C. The individual polygalacturonides are made visible by spraying with a reagent (200 mg of naphthalene-1,3-diol in 50 ml of methanol and 50 ml of 20% (g/g) sulfuric acid). Fractions of equal composition are pooled, and the polygalacturonides contained in these fractions are precipitated with double the volume of acetone and separated from the acetone after centrifugation (6000 g, 10 min) to obtain polygalacturonides of well-defined size.

What is claimed is:

1. A method of making a polygalacturonide preparation useful as a food additive, said method comprising the following steps:
   a) subjecting pectinous plant material to a pectin extraction in an aqueous medium to obtain a suspension comprising of a liquid phase comprising dissolved pectin and solids from the plant material;
   b) removing the solids from the suspension to obtain a liquid material;
   c) precipitating the pectin from the liquid material to obtain a pectin precipitate;
   d) dissolving the pectin precipitate in an aqueous medium and cleaving the dissolved pectin with purified endo-polygalacturonase to obtain polygalacturonides; and thereafter
   e) processing the polygalacturonides obtained in step d) into the polygalacturonide preparation without using an additional separation step and without hydrolyzing any ester groups that are present.

2. The method according to claim 1, wherein the pectin is precipitated by adding $C_1$–$C_{10}$ alkylalcohols and/or inorganic salts.

3. The method according to claim 1, wherein step d) is conducted at a pH of from 1.4 to 8.2.

4. The method according to claim 1, wherein the endo-polygalacturonase is purified using gel filtration.

5. The method according to claim 1, wherein from 10 to 1000 units of endo-polygalacturonase per gram of pectin is used in step d).

6. The method according to claim 1, wherein the endo-polygalacturonase is immobilized.

7. The method according to claim 1, wherein the dissolved pectin is cleaved with the purified endo-polygalacturonase in step d) at 4 to 80° C. for 2 to 300 min.

8. The method according to claim 3, wherein step d) is conducted at a pH of from 3.5 to 5.0.

9. The method according to claim 5, wherein from 20 to 400 units of endo-polygalacturonase per gram of pectin is used in step d).

10. The method according to claim 7, wherein the dissolved pectin is cleaved with the purified endo-polygalacturonase in step d) at 30 to 70° C.

11. The method according to claim 10, wherein the dissolved pectin is cleaved with the purified endo-polygalacturonase in step d) for 45 to 150 min.

12. The method according to claim 2, wherein step d) is conducted at a pH of from 1.4 to 8.2.

13. The method according to claim 2, wherein the endo-polygalacturonase is purified using gel filtration.

14. The method according to claim 2, wherein from 10 to 1000 units of endo-polygalacturonase per gram of pectin is used in step d).

15. The method according to claim 2, wherein the endo-polygalacturonase is immobilized.

16. The method according to claim 2, wherein the dissolved pectin is cleaved with the purified endo-polygalacturonase in step d) at 4 to 80° C. for 2 to 300 min.

17. The method according to claim 3, wherein the endo-polygalacturonase is purified using gel filtration.

18. The method according to claim 3, wherein from 10 to 1000 units of endo-polygalacturonase per gram of pectin is used in step d).

19. The method according to claim 3, wherein the endo-polygalacturonase is immobilized.

20. The method according to claim 3, wherein the dissolved pectin is cleaved with the purified endo-polygalacturonase in step d) at 4 to 80° C. for 2 to 300 min.

21. The method according to claim 4, wherein from 10 to 1000 units of endo-polygalacturonase per gram of pectin is used in step d).

22. The method according to claim 4, wherein the endo-polygalacturonase is immobilized.

23. The method according to claim 4, wherein the dissolved pectin is cleaved with the purified endo-polygalacturonase in step d) at 4 to 80° C. for 2 to 300 min.

24. The method according to claim 5, wherein the endo-polygalacturonase is immobilized.

25. The method according to claim 5, wherein the dissolved pectin is cleaved with the purified endo-polygalacturonase in step d) at 4 to 80° C. for 2 to 300 min.

26. The method according to claim 6, wherein the dissolved pectin is cleaved with the purified endo-polygalacturonase in step d) at 4 to 80° C. for 2 to 300 min.

27. A composition comprising a food and a health promoting agent consisting essentially of polygalacturonides obtained by the process of claim 1.

28. The composition according to claim 27, wherein the food is beverage.

29. The composition according to claim 27, wherein the food is baby food.

30. The composition according to claim 27, wherein the food is canned food.

31. The composition according to claim 27, wherein the polygalacturonides improve the taste of the food.

* * * * *

UNITED STATES PATENT AND TRADEMARK OFFICE
CERTIFICATE OF CORRECTION

PATENT NO. : 6,696,554 B2 Page 1 of 1
APPLICATION NO. : 10/009055
DATED : February 24, 2004
INVENTOR(S) : Christine Lang et al.

It is certified that error appears in the above-identified patent and that said Letters Patent is hereby corrected as shown below:

<u>In the claims</u>:
Col. 8, Line 47-58
Delete claims 27-31.

Signed and Sealed this

Eighteenth Day of July, 2006

JON W. DUDAS
*Director of the United States Patent and Trademark Office*